(12) United States Patent
Berjeaud et al.

(10) Patent No.: US 7,238,515 B2
(45) Date of Patent: * Jul. 3, 2007

(54) **ANTI-*LISTERIA* BACTERIOCIN**

(75) Inventors: Jean-Marie Berjeaud, Savigny L'Evescault (FR); Christophe Fremaux, Poitiers (FR); Yves Cenatiempo, Saint Julien L'Ars (FR); Laurence Simon, Vivonne (FR)

(73) Assignee: Rhodia Chimie, Aubervilliers (FR)

( * ) Notice: Subject to any disclaimer, the term of this patent is extended or adjusted under 35 U.S.C. 154(b) by 117 days.

This patent is subject to a terminal disclaimer.

(21) Appl. No.: 11/028,505

(22) Filed: Jan. 4, 2005

(65) Prior Publication Data

US 2005/0232910 A1    Oct. 20, 2005

Related U.S. Application Data

(62) Division of application No. 10/296,723, filed as application No. PCT/FR01/01642 on May 28, 2001, now Pat. No. 6,855,518.

(30) Foreign Application Priority Data

May 29, 2000 (FR) .................................. 00 06859
Oct. 19, 2000 (FR) .................................. 00 13407

(51) Int. Cl.
    *C12N 1/20* (2006.01)
(52) U.S. Cl. ..................................................... 435/252.3
(58) Field of Classification Search .............. 435/252.3
    See application file for complete search history.

(56) References Cited

OTHER PUBLICATIONS

U. Schillinger et al., "Behaviour of *Listeria monocytogenes* in meat and its control by bacteriocin-producing strain of *Lactobacillus sake*", Journal of Applied Bacteriology, 1991, 70, 473-478.
M.T. Aymerich et al., "Bacteriocin-producing lactobacilli in Spanish-style fermented sausages: characterization of bacteriocins", Food Microbiology, 2000, 17, 33-45.

*Primary Examiner*—Karen Cochrane Carlson
(74) *Attorney, Agent, or Firm*—Buchanan, Ingersoll & Rooney, PC

(57) ABSTRACT

The invention concerns an isolated polypeptide which is a bacteriocin called Sakacin G derived from *Lactobacillus sakei* 2512. The invention also concerns a nucleic acid molecule encoding for said bacteriocin and the use of said polypeptide as an active agent against pathogenic and undesirable flora in the preparation of food products.

3 Claims, 2 Drawing Sheets

FIG. 2

SEQUENCE LISTING

```
<160> NUMBER OF SEQ ID NOS: 18

<210> SEQ ID NO 1
<211> LENGTH: 196
<212> TYPE: DNA
<213> ORGANISM: Lactobacillus sake
<220> FEATURE:
<221> NAME/KEY: CDS
<222> LOCATION: (20)..(187)

<400> SEQUENCE: 1
ttaacaggag gtattcaaa atg aag aat aca cgt agc tta acg atc caa gaa       52
                     Met Lys Asn Thr Arg Ser Leu Thr Ile Gln Glu
                       1               5                  10 ata aaa tcc atc aca ggt ggt aaa tac tat ggt aat ggt gtt agc tgt      100
Ile Lys Ser Ile Thr Gly Gly Lys Tyr Tyr Gly Asn Gly Val Ser Cys
             15                  20                  25 aac tct cat ggt tgt tca gta aat tgg ggg caa gca tgg act tgt ggg      148
Asn Ser His Gly Cys Ser Val Asn Trp Gly Gln Ala Trp Thr Cys Gly
         30                  35                  40
```

```
gta aat cat cta gct aat ggc ggt cat ggg gtt tgt taa ttatttaaa        196
Val Asn His Leu Ala Asn Gly Gly His Gly Val Cys
         45                  50                  55
```

<210> SEQ ID NO 2
<211> LENGTH: 55
<212> TYPE: PRT
<213> ORGANISM: Lactobacillus sake

<400> SEQUENCE: 2

```
Met Lys Asn Thr Arg Ser Leu Thr Ile Gln Glu Ile Lys Ser Ile Thr
 1               5                  10                  15

Gly Gly Lys Tyr Tyr Gly Asn Gly Val Ser Cys Asn Ser His Gly Cys
             20                  25                  30

Ser Val Asn Trp Gly Gln Ala Trp Thr Cys Gly Val Asn His Leu Ala
         35                  40                  45

Asn Gly Gly His Gly Val Cys
     50                  55
```

<210> SEQ ID NO 3
<211> LENGTH: 196
<212> TYPE: DNA
<213> ORGANISM: Lactobacillus sake
<220> FEATURE:
<221> NAME/KEY: CDS
<222> LOCATION: (20)..(187)

<400> SEQUENCE: 3

```
taatttggag atgttctttt atg aaa aac gca aaa agc cta aca att caa gaa         52
                     Met Lys Asn Ala Lys Ser Leu Thr Ile Gln Glu
                      1               5                  10 atg aaa tct att aca ggt ggt aaa tac tat ggt aat ggc gtt agc tgt        100
Met Lys Ser Ile Thr Gly Gly Lys Tyr Tyr Gly Asn Gly Val Ser Cys
             15                  20                  25 aac tct cac ggc tgt tca gta aat tgg ggg caa gca tgg act tgt gga        148
Asn Ser His Gly Cys Ser Val Asn Trp Gly Gln Ala Trp Thr Cys Gly
         30                  35                  40 gta aac cat cta gct aat ggc ggt cat gga gtt tgt taa ttaccagat          196
Val Asn His Leu Ala Asn Gly Gly His Gly Val Cys
     45                  50                  55
```

<210> SEQ ID NO 4
<211> LENGTH: 55
<212> TYPE: PRT
<213> ORGANISM: Lactobacillus sake

<400> SEQUENCE: 4

```
Met Lys Asn Ala Lys Ser Leu Thr Ile Gln Glu Met Lys Ser Ile Thr
 1               5                  10                  15

Gly Gly Lys Tyr Tyr Gly Asn Gly Val Ser Cys Asn Ser His Gly Cys
             20                  25                  30

Ser Val Asn Trp Gly Gln Ala Trp Thr Cys Gly Val Asn His Leu Ala
         35                  40                  45

Asn Gly Gly His Gly Val Cys
     50                  55
```

<210> SEQ ID NO 5
<211> LENGTH: 181
<212> TYPE: DNA
<213> ORGANISM: Lactobacillus sake
<220> FEATURE:
<221> NAME/KEY: CDS
<222> LOCATION: (24)..(179)

```
<400> SEQUENCE: 5
ttaaaaaagg agacgtgatt aaa atg gca aac aaa gac aat att aaa act gaa      53
                      Met Ala Asn Lys Asp Asn Ile Lys Thr Glu
                        1               5                  10 tct aaa aac aac atc gaa gct ctc ttg cac tta cta gaa aag cgt cct       101
Ser Lys Asn Asn Ile Glu Ala Leu Leu His Leu Leu Glu Lys Arg Pro
             15                  20                  25 gta aaa tcc agt gaa tta ctc gat att att gac gtt ctt tcc caa gtt       149
Val Lys Ser Ser Glu Leu Leu Asp Ile Ile Asp Val Leu Ser Gln Val
         30                  35                  40 tat agc aaa att gat ata gct aag aat ccc ga                            181
Tyr Ser Lys Ile Asp Ile Ala Lys Asn Pro
     45                  50

<210> SEQ ID NO 6
<211> LENGTH: 52
<212> TYPE: PRT
<213> ORGANISM: Lactobacillus sake

<400> SEQUENCE: 6

Met Ala Asn Lys Asp Asn Ile Lys Thr Glu Ser Lys Asn Asn Ile Glu
  1               5                  10                  15

Ala Leu Leu His Leu Leu Glu Lys Arg Pro Val Lys Ser Ser Glu Leu
             20                  25                  30

Leu Asp Ile Ile Asp Val Leu Ser Gln Val Tyr Ser Lys Ile Asp Ile
         35                  40                  45

Ala Lys Asn Pro
         50

<210> SEQ ID NO 7
<211> LENGTH: 1203
<212> TYPE: DNA
<213> ORGANISM: Lactobacillus sake
<220> FEATURE:
<221> NAME/KEY: CDS
<222> LOCATION: (20)..(1201)

<400> SEQUENCE: 7
aaattaggag acttatata ttg ttt aat ctg ttg aga tac aaa aaa tta tat      52
                    Leu Phe Asn Leu Leu Arg Tyr Lys Lys Leu Tyr
                      1               5                  10 tgt tca caa gtg gat gaa gat gat tgt gga atc gca gct ttg aat atg      100
Cys Ser Gln Val Asp Glu Asp Asp Cys Gly Ile Ala Ala Leu Asn Met
             15                  20                  25 att ttt aaa aat ttt ggt tcc gaa tat tca cta tca aaa ttg cga ttc      148
Ile Phe Lys Asn Phe Gly Ser Glu Tyr Ser Leu Ser Lys Leu Arg Phe
         30                  35                  40 tta gca aaa acc agt caa caa ggg act act att ttt gga ctg ata aag      196
Leu Ala Lys Thr Ser Gln Gln Gly Thr Thr Ile Phe Gly Leu Ile Lys
     45                  50                  55 gct gca gag gaa cta aat tta gaa gcg aat gca tta caa gct gat atg      244
Ala Ala Glu Glu Leu Asn Leu Glu Ala Asn Ala Leu Gln Ala Asp Met
 60                  65                  70                  75 ggc atc ttt aaa gat gaa aat tta atg cta cca atc att gca cat gtt      292
Gly Ile Phe Lys Asp Glu Asn Leu Met Leu Pro Ile Ile Ala His Val
                 80                  85                  90 tta aag caa gga aaa gtt ctg cat tac tac gtt gta ttt gat gtt tcg      340
Leu Lys Gln Gly Lys Val Leu His Tyr Tyr Val Val Phe Asp Val Ser
             95                 100                 105 aaa gac ttt tta att att ggt gac cca gac cca aca ata gga att acg      388
Lys Asp Phe Leu Ile Ile Gly Asp Pro Asp Pro Thr Ile Gly Ile Thr
```

|     |     |     |     |     |     |     |     |     |     |     |     |     |
|---|---|---|---|---|---|---|---|---|---|---|---|---|
| Lys | Asp | Phe | Leu | Ile | Ile | Gly | Asp | Pro | Asp | Pro | Thr | Ile | Gly | Ile | Thr |
|  | 110 |  |  |  | 115 |  |  |  | 120 |  |  |

```
gaa atc tcc aaa aag gat ttt gaa aat gaa tgg acg ggt aat ttc ata      436
Glu Ile Ser Lys Lys Asp Phe Glu Asn Glu Trp Thr Gly Asn Phe Ile
    125             130                 135 aca ttt tca aaa gga aag aac ttt gtt tca gag aag cag aga aat aac      484
Thr Phe Ser Lys Gly Lys Asn Phe Val Ser Glu Lys Gln Arg Asn Asn
140             145                 150                 155 agt tta ctc aag ttt att cct att ttg aga cag caa aaa tcc cta ata      532
Ser Leu Leu Lys Phe Ile Pro Ile Leu Arg Gln Gln Lys Ser Leu Ile
                160                 165                 170 ttc tgg ata gct ttc gcc gca ata cta ttg atg ata att agt att gca      580
Phe Trp Ile Ala Phe Ala Ala Ile Leu Leu Met Ile Ile Ser Ile Ala
            175                 180                 185 gga tca ctt ttt tta gaa caa ctt gta gat ata tat ata cca cac aaa      628
Gly Ser Leu Phe Leu Glu Gln Leu Val Asp Ile Tyr Ile Pro His Lys
        190                 195                 200 aat atg gat aca ttg ggg att atc tcg att tgc tta att gga gcc tat      676
Asn Met Asp Thr Leu Gly Ile Ile Ser Ile Cys Leu Ile Gly Ala Tyr
    205                 210                 215 ctt tta cag gcc gta atg acg tat ttt cag aat ttt tta cta act ata      724
Leu Leu Gln Ala Val Met Thr Tyr Phe Gln Asn Phe Leu Leu Thr Ile
220             225                 230                 235 ttt gga caa aat ctt tct aga aaa att att tta aat tat att aat cac      772
Phe Gly Gln Asn Leu Ser Arg Lys Ile Ile Leu Asn Tyr Ile Asn His
                240                 245                 250 ctt ttt gaa tta ccc atg tct ttc ttc tca aca cgt aga gtt ggc gaa      820
Leu Phe Glu Leu Pro Met Ser Phe Phe Ser Thr Arg Arg Val Gly Glu
            255                 260                 265 ata gtc tct cgg ttt aca gat gca agc aag att ata gat gct ttg gca      868
Ile Val Ser Arg Phe Thr Asp Ala Ser Lys Ile Ile Asp Ala Leu Ala
        270                 275                 280 agt acg att ttg act ctc ttt tta gat gtt tgg atg ttg gtt aca atc      916
Ser Thr Ile Leu Thr Leu Phe Leu Asp Val Trp Met Leu Val Thr Ile
    285                 290                 295 tca atc gtt ctc gta ttt tta aat aca aag tta ttt atg att tct ctg      964
Ser Ile Val Leu Val Phe Leu Asn Thr Lys Leu Phe Met Ile Ser Leu
300             305                 310                 315 gta tct ata ccg gtg tac tca gtt ata att tat gcg ttt aaa aat aca     1012
Val Ser Ile Pro Val Tyr Ser Val Ile Ile Tyr Ala Phe Lys Asn Thr
                320                 325                 330 ttt aat ggc ctg aac cat aaa tca atg gaa aat gca gca tta ttg aat     1060
Phe Asn Gly Leu Asn His Lys Ser Met Glu Asn Ala Ala Leu Leu Asn
            335                 340                 345 tct gca ata atc gaa aac gta act ggc ata gaa act gta aaa tca tta     1108
Ser Ala Ile Ile Glu Asn Val Thr Gly Ile Glu Thr Val Lys Ser Leu
        350                 355                 360 act tca gaa gaa ttt tcc tac aat caa atc act gat aga ttc gaa aat     1156
Thr Ser Glu Glu Phe Ser Tyr Asn Gln Ile Thr Asp Arg Phe Glu Asn
    365                 370                 375 ttt ctt aac agt tcc tta cgg tat acg ata gct gac caa gga cag ca      1203
Phe Leu Asn Ser Ser Leu Arg Tyr Thr Ile Ala Asp Gln Gly Gln
380                 385                 390
```

<210> SEQ ID NO 8
<211> LENGTH: 394
<212> TYPE: PRT
<213> ORGANISM: Lactobacillus sake

<400> SEQUENCE: 8

```
Leu Phe Asn Leu Leu Arg Tyr Lys Lys Leu Tyr Cys Ser Gln Val Asp
 1               5                  10                  15

Glu Asp Asp Cys Gly Ile Ala Ala Leu Asn Met Ile Phe Lys Asn Phe
            20                  25                  30

Gly Ser Glu Tyr Ser Leu Ser Lys Leu Arg Phe Leu Ala Lys Thr Ser
        35                  40                  45

Gln Gln Gly Thr Thr Ile Phe Gly Leu Ile Lys Ala Ala Glu Glu Leu
    50                  55                  60

Asn Leu Glu Ala Asn Ala Leu Gln Ala Asp Met Gly Ile Phe Lys Asp
 65                  70                  75                  80

Glu Asn Leu Met Leu Pro Ile Ile Ala His Val Leu Lys Gln Gly Lys
                85                  90                  95

Val Leu His Tyr Tyr Val Val Phe Asp Val Ser Lys Asp Phe Leu Ile
            100                 105                 110

Ile Gly Asp Pro Asp Pro Thr Ile Gly Ile Thr Glu Ile Ser Lys Lys
        115                 120                 125

Asp Phe Glu Asn Glu Trp Thr Gly Asn Phe Ile Thr Phe Ser Lys Gly
    130                 135                 140

Lys Asn Phe Val Ser Glu Lys Gln Arg Asn Asn Ser Leu Leu Lys Phe
145                 150                 155                 160

Ile Pro Ile Leu Arg Gln Gln Lys Ser Leu Ile Phe Trp Ile Ala Phe
                165                 170                 175

Ala Ala Ile Leu Leu Met Ile Ile Ser Ile Ala Gly Ser Leu Phe Leu
            180                 185                 190

Glu Gln Leu Val Asp Ile Tyr Ile Pro His Lys Asn Met Asp Thr Leu
    195                 200                 205

Gly Ile Ile Ser Ile Cys Leu Ile Gly Ala Tyr Leu Leu Gln Ala Val
210                 215                 220

Met Thr Tyr Phe Gln Asn Phe Leu Leu Thr Ile Phe Gly Gln Asn Leu
225                 230                 235                 240

Ser Arg Lys Ile Ile Leu Asn Tyr Ile Asn His Leu Phe Glu Leu Pro
                245                 250                 255

Met Ser Phe Phe Ser Thr Arg Arg Val Gly Glu Ile Val Ser Arg Phe
            260                 265                 270

Thr Asp Ala Ser Lys Ile Ile Asp Ala Leu Ala Ser Thr Ile Leu Thr
    275                 280                 285

Leu Phe Leu Asp Val Trp Met Leu Val Thr Ile Ser Ile Val Leu Val
290                 295                 300

Phe Leu Asn Thr Lys Leu Phe Met Ile Ser Leu Val Ser Ile Pro Val
305                 310                 315                 320

Tyr Ser Val Ile Ile Tyr Ala Phe Lys Asn Thr Phe Asn Gly Leu Asn
                325                 330                 335

His Lys Ser Met Glu Asn Ala Ala Leu Leu Asn Ser Ala Ile Ile Glu
            340                 345                 350

Asn Val Thr Gly Ile Glu Thr Val Lys Ser Leu Thr Ser Glu Glu Phe
    355                 360                 365

Ser Tyr Asn Gln Ile Thr Asp Arg Phe Glu Asn Phe Leu Asn Ser Ser
370                 375                 380

Leu Arg Tyr Thr Ile Ala Asp Gln Gly Gln
385                 390
```

<210> SEQ ID NO 9
<211> LENGTH: 2042
<212> TYPE: DNA

-continued

<213> ORGANISM: Lactobacillus sake

<400> SEQUENCE: 9

```
agcttcggga ttcttagcta tatcaattt  gctataaact  tgggaaagaa  cgtcaataat      60
atcgagtaat tcactggatt ttacaggacg cttttctagt aagtgcaaga gagcttcgat     120
gttgttttta gattcagttt taatattgtc tttgtttgcc attttaatca cgtctccttt     180
tttatagtaa taaaaaaaac acaattaaat tagtgctttt ttatctggta attaacaaac     240
tccatgaccg ccattagcta gatggtttac tccacaagtc catgcttgcc cccaatttac     300
tgaacagccg tgagagttac agctaacgcc attaccatag tatttaccac ctgtaataga     360
tttcatttct tgaattgtta ggcttttgc  gttttttcata aagaacatct ccaaattata     420
tttttttagtg attcttgaag ttctgttgta acgcagaatt ttggaagaat gagtacttgt    480
tagaaatttg ccgatttaaa taattaacaa accccatgac cgccattagc tagatgattt     540
accccacaag tccatgcttg ccccaattt  actgaacaac catgagagtt acagctaaca     600
ccattaccat agtatttacc acctgtgatg gattttattt cttggatcgt taagctacgt     660
gtattcttca ttttgaatac ctcctgttaa ataattttta cacgatcagt gtagttctaa     720
tgtgaaattg tgtcaagttt agcaaatata tattttaggc atggaaaaac ttgcttttaa     780
ttcgacttga ctataacggt ataatactgg tattactata tttgtttagc ttcacaaaaa     840
aattaggaga cttatatatt gtttaatctg ttgagataca aaaaattata ttgttcacaa     900
gtggatgaag atgattgtgg aatcgcagct ttgaatatga tttttaaaaa ttttggttcc     960
gaatattcac tatcaaaatt gcgattctta gcaaaaacca gtcaacaagg gactactatt    1020
tttggactga taaaggctgc agaggaacta aatttagaag cgaatgcatt acaagctgat    1080
atgggcatct ttaaagatga aaatttaatg ctaccaatca ttgcacatgt tttaaagcaa    1140
ggaaaagttc tgcattacta cgttgtattt gatgtttcga aagactttt  aattattggt    1200
gacccagacc caacaatagg aattacggaa atctccaaaa aggattttga aaatgaatgg    1260
acgggtaatt tcataacatt ttcaaaagga aagaactttg tttcagagaa gcagagaaat    1320
aacagtttac tcaagtttat tcctatttg  agacagcaaa aatccctaat attctggata    1380
gctttcgccg caatactatt gatgataatt agtattgcag gatcactttt tttagaacaa    1440
cttgtagata tatatatacc acacaaaaat atggatacat tggggattat ctcgatttgc    1500
ttaattggag cctatctttt acaggccgta atgacgtatt ttcagaattt tttactaact    1560
atatttggac aaaatctttc tagaaaaatt attttaaatt atattaatca ccttttttgaa    1620
ttacccatgt ctttcttctc aacacgtaga gttggcgaaa tagtctctcg gtttacagat    1680
gcaagcaaga ttatagatgc tttggcaagt acgattttga ctctcttttt agatgtttgg    1740
atgttggtta caatctcaat cgttctcgta tttttaaata caaagttatt tatgatttct    1800
ctggtatcta taccggtgta ctcagttata atttatgcgt ttaaaaatac atttaatggc    1860
ctgaaccata aatcaatgga aaatgcagca ttattgaatt ctgcaataat cgaaaacgta    1920
actggcatag aaactgtaaa atcattaact tcagaagaat tttcctacaa tcaaatcact    1980
gatagattcg aaaattttct taacagttcc ttacggtata cgatagctga ccaaggacag    2040
ca                                                                  2042
```

<210> SEQ ID NO 10
<211> LENGTH: 20
<212> TYPE: DNA
<213> ORGANISM: Lactobacillus sake -continued

```
<220> FEATURE:
<221> NAME/KEY: modified_base
<222> LOCATION: (12)
<223> OTHER INFORMATION: a, c, g, t, unknown, or other
<220> FEATURE:
<221> NAME/KEY: modified_base
<222> LOCATION: (18)
<223> OTHER INFORMATION: a, c, g, t, unknown, or other

<400> SEQUENCE: 10
aartattatg gnaayggngt                                              20

<210> SEQ ID NO 11
<211> LENGTH: 20
<212> TYPE: DNA
<213> ORGANISM: Lactobacillus sake
<220> FEATURE:
<221> NAME/KEY: modified_base
<222> LOCATION: (9)
<223> OTHER INFORMATION: a, c, g, t, unknown, or other
<220> FEATURE:
<221> NAME/KEY: modified_base
<222> LOCATION: (12)
<223> OTHER INFORMATION: a, c, g, t, unknown, or other
<220> FEATURE:
<221> NAME/KEY: modified_base
<222> LOCATION: (18)
<223> OTHER INFORMATION: a, c, g, t, unknown, or other

<400> SEQUENCE: 11
acatgatgnc nccrttngc                                               20

<210> SEQ ID NO 12
<211> LENGTH: 37
<212> TYPE: PRT
<213> ORGANISM: Lactobacillus sake

<400> SEQUENCE: 12

Lys Tyr Tyr Gly Asn Gly Val Ser Cys Asn Ser His Gly Cys Ser Val
 1               5                  10                  15

Asn Trp Gly Gln Ala Trp Thr Cys Gly Val Asn His Leu Ala Asn Gly
            20                  25                  30

Gly His Gly Val Cys
        35

<210> SEQ ID NO 13
<211> LENGTH: 2214
<212> TYPE: DNA
<213> ORGANISM: Lactobacillus sake
<220> FEATURE:
<221> NAME/KEY: CDS
<222> LOCATION: (20)..(2200)

<400> SEQUENCE: 13
aaattaggag acttatata ttg ttt aat ctg ttg aga tac aaa aaa tta tat    52
                    Leu Phe Asn Leu Leu Arg Tyr Lys Lys Leu Tyr
                     1               5                  10 tgt tca caa gtg gat gaa gat gat tgt gga atc gca gct ttg aat atg   100
Cys Ser Gln Val Asp Glu Asp Asp Cys Gly Ile Ala Ala Leu Asn Met
         15                  20                  25 att ttt aaa aat ttt ggt tcc gaa tat tca cta tca aaa ttg cga ttc   148
Ile Phe Lys Asn Phe Gly Ser Glu Tyr Ser Leu Ser Lys Leu Arg Phe
     30                  35                  40 tta gca aaa acc agt caa caa ggg act act att ttt gga ctg ata aag   196
Leu Ala Lys Thr Ser Gln Gln Gly Thr Thr Ile Phe Gly Leu Ile Lys
 45                  50                  55
```

| | |
|---|---|
| gct gca gag gaa cta aat tta gaa gcg aat gca tta caa gct gat atg<br>Ala Ala Glu Glu Leu Asn Leu Glu Ala Asn Ala Leu Gln Ala Asp Met<br>60                     65                     70                    75 | 244 |
| ggc atc ttt aaa gat gaa aat tta atg cta cca atc att gca cat gtt<br>Gly Ile Phe Lys Asp Glu Asn Leu Met Leu Pro Ile Ile Ala His Val<br>                  80                     85                     90 | 292 |
| tta aag caa gga aaa gtt ctg cat tac tac gtt gta ttt gat gtt tcg<br>Leu Lys Gln Gly Lys Val Leu His Tyr Tyr Val Val Phe Asp Val Ser<br>                  95                    100                 105 | 340 |
| aaa gac ttt tta att att ggt gac cca gac cca aca ata gga att acg<br>Lys Asp Phe Leu Ile Ile Gly Asp Pro Asp Pro Thr Ile Gly Ile Thr<br>110                     115                    120 | 388 |
| gaa atc tcc aaa aag gat ttt gaa aat gaa tgg acg ggt aat ttc ata<br>Glu Ile Ser Lys Lys Asp Phe Glu Asn Glu Trp Thr Gly Asn Phe Ile<br>125                     130                    135 | 436 |
| aca ttt tca aaa gga aag aac ttt gtt tca gag aag cag aga aat aac<br>Thr Phe Ser Lys Gly Lys Asn Phe Val Ser Glu Lys Gln Arg Asn Asn<br>140                     145                    150                155 | 484 |
| agt tta ctc aag ttt att cct att ttg aga cag caa aaa tcc cta ata<br>Ser Leu Leu Lys Phe Ile Pro Ile Leu Arg Gln Gln Lys Ser Leu Ile<br>                      160                    165                 170 | 532 |
| ttc tgg ata gct ttc gcc gca ata cta ttg atg ata att agt att gca<br>Phe Trp Ile Ala Phe Ala Ala Ile Leu Leu Met Ile Ile Ser Ile Ala<br>                  175                    180                 185 | 580 |
| gga tca ctt ttt tta gaa caa ctt gta gat ata tat ata cca cac aaa<br>Gly Ser Leu Phe Leu Glu Gln Leu Val Asp Ile Tyr Ile Pro His Lys<br>                  190                    195                 200 | 628 |
| aat atg gat aca ttg ggg att atc tcg att tgc tta att gga gcc tat<br>Asn Met Asp Thr Leu Gly Ile Ile Ser Ile Cys Leu Ile Gly Ala Tyr<br>205                     210                    215 | 676 |
| ctt tta cag gcc gta atg acg tat ttt cag aat ttt tta cta act ata<br>Leu Leu Gln Ala Val Met Thr Tyr Phe Gln Asn Phe Leu Leu Thr Ile<br>220                     225                    230                235 | 724 |
| ttt gga caa aat ctt tct aga aaa att att tta aat tat att aat cac<br>Phe Gly Gln Asn Leu Ser Arg Lys Ile Ile Leu Asn Tyr Ile Asn His<br>                      240                    245                 250 | 772 |
| ctt ttt gaa tta ccc atg tct ttc ttc tca aca cgt aga gtt ggc gaa<br>Leu Phe Glu Leu Pro Met Ser Phe Phe Ser Thr Arg Arg Val Gly Glu<br>                  255                    260                 265 | 820 |
| ata gtc tct cgg ttt aca gat gca agc aag att ata gat gct ttg gca<br>Ile Val Ser Arg Phe Thr Asp Ala Ser Lys Ile Ile Asp Ala Leu Ala<br>                  270                    275                 280 | 868 |
| agt acg att ttg act ctc ttt tta gat gtt tgg atg ttg gtt aca atc<br>Ser Thr Ile Leu Thr Leu Phe Leu Asp Val Trp Met Leu Val Thr Ile<br>285                     290                    295 | 916 |
| tca atc gtt ctc gta ttt tta aat aca aag tta ttt atg att tct ctg<br>Ser Ile Val Leu Val Phe Leu Asn Thr Lys Leu Phe Met Ile Ser Leu<br>300                     305                    310                315 | 964 |
| gta tct ata ccg gtg tac tca gtt ata att tat gcg ttt aaa aat aca<br>Val Ser Ile Pro Val Tyr Ser Val Ile Ile Tyr Ala Phe Lys Asn Thr<br>                  320                    325                 330 | 1012 |
| ttt aat ggc ctg aac cat aaa tca atg gaa aat gca gca tta ttg aat<br>Phe Asn Gly Leu Asn His Lys Ser Met Glu Asn Ala Ala Leu Leu Asn<br>                  335                    340                 345 | 1060 |
| tct gca ata atc gaa aac gta act ggc ata gaa act gta aaa tca tta<br>Ser Ala Ile Ile Glu Asn Val Thr Gly Ile Glu Thr Val Lys Ser Leu<br>                  350                    355                 360 | 1108 |
| act tca gaa gaa ttt tcc tac aat caa atc act gat aga ttc gaa aat<br>Thr Ser Glu Glu Phe Ser Tyr Asn Gln Ile Thr Asp Arg Phe Glu Asn<br>365                     370                    375 | 1156 |

```
                                                           -continued ttt ctt aac agt tcc tta cgg tat acg ata gct gac caa gga cag caa      1204
Phe Leu Asn Ser Ser Leu Arg Tyr Thr Ile Ala Asp Gln Gly Gln Gln
380                 385                 390                 395 gct tta aaa gtg ggt ttg aag cta att ctt ata gtc ttt atc tta tgg      1252
Ala Leu Lys Val Gly Leu Lys Leu Ile Leu Ile Val Phe Ile Leu Trp
                400                 405                 410 gct gga gca atc caa gtt atg agg ggg aat ctc aca gtc gga aga tta      1300
Ala Gly Ala Ile Gln Val Met Arg Gly Asn Leu Thr Val Gly Arg Leu
            415                 420                 425 ttg gct ttt aat gct tta gta aca tac ttt tta aat ccc tta gag aat      1348
Leu Ala Phe Asn Ala Leu Val Thr Tyr Phe Leu Asn Pro Leu Glu Asn
        430                 435                 440 att att aat tta caa cca aag cta caa act gca aga gtc gct aat att      1396
Ile Ile Asn Leu Gln Pro Lys Leu Gln Thr Ala Arg Val Ala Asn Ile
    445                 450                 455 aga cta aat gaa gta tta tta gtg gat tct gag ttt aat agg ggg gga      1444
Arg Leu Asn Glu Val Leu Leu Val Asp Ser Glu Phe Asn Arg Gly Gly
460                 465                 470                 475 cgc gac agc tca aca aac tta aat ggg gat atc gta ttt caa gat gta      1492
Arg Asp Ser Ser Thr Asn Leu Asn Gly Asp Ile Val Phe Gln Asp Val
                480                 485                 490 gaa ttt agt tat ggt tac gga tcg aac gta ttg cac aac atc aat ata      1540
Glu Phe Ser Tyr Gly Tyr Gly Ser Asn Val Leu His Asn Ile Asn Ile
            495                 500                 505 aaa ata caa aag aat agt agt aca acg att gtt ggt atg agc ggt tct      1588
Lys Ile Gln Lys Asn Ser Ser Thr Thr Ile Val Gly Met Ser Gly Ser
        510                 515                 520 ggg aaa tcc aca tta gca aaa tta atg gtt ggt ttc tat caa gcc gga      1636
Gly Lys Ser Thr Leu Ala Lys Leu Met Val Gly Phe Tyr Gln Ala Gly
    525                 530                 535 tca gga caa ata tta tta aat ggt aaa tta atc gat aac att gat cgt      1684
Ser Gly Gln Ile Leu Leu Asn Gly Lys Leu Ile Asp Asn Ile Asp Arg
540                 545                 550                 555 cat gcc ctg aga caa tcg att acg tat gta cca cag gaa ccg gta atg      1732
His Ala Leu Arg Gln Ser Ile Thr Tyr Val Pro Gln Glu Pro Val Met
                560                 565                 570 ttc gca ggt aca att tta gaa aat ctt att atg cag aat aaa aga aat      1780
Phe Ala Gly Thr Ile Leu Glu Asn Leu Ile Met Gln Asn Lys Arg Asn
            575                 580                 585 tta tct att gat aaa gtg aaa gag gca tgt agg ata gcc gaa att gat      1828
Leu Ser Ile Asp Lys Val Lys Glu Ala Cys Arg Ile Ala Glu Ile Asp
        590                 595                 600 aaa gat ata gaa aat ttt cct atg ggg tat gat aca gat att tcc gaa      1876
Lys Asp Ile Glu Asn Phe Pro Met Gly Tyr Asp Thr Asp Ile Ser Glu
    605                 610                 615 cat ggg agt tca atc tca gta ggt caa aaa caa aga ctt tct att gca      1924
His Gly Ser Ser Ile Ser Val Gly Gln Lys Gln Arg Leu Ser Ile Ala
620                 625                 630                 635 aga tca ctg ctg aca gag tct aat gtt tta ctg ttt gat gaa tca acc      1972
Arg Ser Leu Leu Thr Glu Ser Asn Val Leu Leu Phe Asp Glu Ser Thr
                640                 645                 650 agt agt ttg gac act att act gag cag cga ata att gaa aac cta ttg      2020
Ser Ser Leu Asp Thr Ile Thr Glu Gln Arg Ile Ile Glu Asn Leu Leu
            655                 660                 665 aat tta aat gac aaa aca tta ata ttc gtt gca cat cga ttg tca gtt      2068
Asn Leu Asn Asp Lys Thr Leu Ile Phe Val Ala His Arg Leu Ser Val
        670                 675                 680 gct aag caa act gaa aat att atc gtt atg gat cac ggt gga att gtt      2116
Ala Lys Gln Thr Glu Asn Ile Ile Val Met Asp His Gly Gly Ile Val
```

```
                    685             690             695
gaa aca ggt tcg cat gat aaa tta ata ttg gaa aat gga tat tat aaa    2164
Glu Thr Gly Ser His Asp Lys Leu Ile Leu Glu Asn Gly Tyr Tyr Lys
700                 705             710             715 gaa tta tgt act gtg aag acg aag aaa aaa gaa ttt tagataaaac aaaa   2214
Glu Leu Cys Thr Val Lys Thr Lys Lys Lys Glu Phe
                720             725
```

<210> SEQ ID NO 14
<211> LENGTH: 727
<212> TYPE: PRT
<213> ORGANISM: Lactobacillus sake

<400> SEQUENCE: 14

```
Leu Phe Asn Leu Leu Arg Tyr Lys Lys Leu Tyr Cys Ser Gln Val Asp
 1               5                  10                  15

Glu Asp Asp Cys Gly Ile Ala Ala Leu Asn Met Ile Phe Lys Asn Phe
             20                  25                  30

Gly Ser Glu Tyr Ser Leu Ser Lys Leu Arg Phe Leu Ala Lys Thr Ser
         35                  40                  45

Gln Gln Gly Thr Thr Ile Phe Gly Leu Ile Lys Ala Ala Glu Glu Leu
     50                  55                  60

Asn Leu Glu Ala Asn Ala Leu Gln Ala Asp Met Gly Ile Phe Lys Asp
 65                  70                  75                  80

Glu Asn Leu Met Leu Pro Ile Ile Ala His Val Leu Lys Gln Gly Lys
                 85                  90                  95

Val Leu His Tyr Tyr Val Val Phe Asp Val Ser Lys Asp Phe Leu Ile
            100                 105                 110

Ile Gly Asp Pro Asp Pro Thr Ile Gly Ile Thr Glu Ile Ser Lys Lys
        115                 120                 125

Asp Phe Glu Asn Glu Trp Thr Gly Asn Phe Ile Thr Phe Ser Lys Gly
    130                 135                 140

Lys Asn Phe Val Ser Glu Lys Gln Arg Asn Asn Ser Leu Leu Lys Phe
145                 150                 155                 160

Ile Pro Ile Leu Arg Gln Gln Lys Ser Leu Ile Phe Trp Ile Ala Phe
                165                 170                 175

Ala Ala Ile Leu Leu Met Ile Ile Ser Ile Ala Gly Ser Leu Phe Leu
            180                 185                 190

Glu Gln Leu Val Asp Ile Tyr Ile Pro His Lys Asn Met Asp Thr Leu
        195                 200                 205

Gly Ile Ile Ser Ile Cys Leu Ile Gly Ala Tyr Leu Leu Gln Ala Val
    210                 215                 220

Met Thr Tyr Phe Gln Asn Phe Leu Leu Thr Ile Phe Gly Gln Asn Leu
225                 230                 235                 240

Ser Arg Lys Ile Ile Leu Asn Tyr Ile Asn His Leu Phe Glu Leu Pro
                245                 250                 255

Met Ser Phe Phe Ser Thr Arg Arg Val Gly Glu Ile Val Ser Arg Phe
            260                 265                 270

Thr Asp Ala Ser Lys Ile Ile Asp Ala Leu Ala Ser Thr Ile Leu Thr
        275                 280                 285

Leu Phe Leu Asp Val Trp Met Leu Val Thr Ile Ser Ile Val Leu Val
    290                 295                 300

Phe Leu Asn Thr Lys Leu Phe Met Ile Ser Leu Val Ser Ile Pro Val
305                 310                 315                 320

Tyr Ser Val Ile Ile Tyr Ala Phe Lys Asn Thr Phe Asn Gly Leu Asn
```

-continued

```
                325                 330                 335
His Lys Ser Met Glu Asn Ala Ala Leu Leu Asn Ser Ala Ile Ile Glu
                340                 345                 350

Asn Val Thr Gly Ile Glu Thr Val Lys Ser Leu Thr Ser Glu Glu Phe
            355                 360                 365

Ser Tyr Asn Gln Ile Thr Asp Arg Phe Glu Asn Phe Leu Asn Ser Ser
        370                 375                 380

Leu Arg Tyr Thr Ile Ala Asp Gln Gly Gln Gln Ala Leu Lys Val Gly
385                 390                 395                 400

Leu Lys Leu Ile Leu Ile Val Phe Ile Leu Trp Ala Gly Ala Ile Gln
                405                 410                 415

Val Met Arg Gly Asn Leu Thr Val Gly Arg Leu Leu Ala Phe Asn Ala
            420                 425                 430

Leu Val Thr Tyr Phe Leu Asn Pro Leu Glu Asn Ile Ile Asn Leu Gln
        435                 440                 445

Pro Lys Leu Gln Thr Ala Arg Val Ala Asn Ile Arg Leu Asn Glu Val
    450                 455                 460

Leu Leu Val Asp Ser Glu Phe Asn Arg Gly Gly Arg Asp Ser Ser Thr
465                 470                 475                 480

Asn Leu Asn Gly Asp Ile Val Phe Gln Asp Val Glu Phe Ser Tyr Gly
                485                 490                 495

Tyr Gly Ser Asn Val Leu His Asn Ile Asn Ile Lys Ile Gln Lys Asn
            500                 505                 510

Ser Ser Thr Thr Ile Val Gly Met Ser Gly Ser Gly Lys Ser Thr Leu
        515                 520                 525

Ala Lys Leu Met Val Gly Phe Tyr Gln Ala Gly Ser Gly Gln Ile Leu
    530                 535                 540

Leu Asn Gly Lys Leu Ile Asp Asn Ile Asp Arg His Ala Leu Arg Gln
545                 550                 555                 560

Ser Ile Thr Tyr Val Pro Gln Glu Pro Val Met Phe Ala Gly Thr Ile
                565                 570                 575

Leu Glu Asn Leu Ile Met Gln Asn Lys Arg Asn Leu Ser Ile Asp Lys
            580                 585                 590

Val Lys Glu Ala Cys Arg Ile Ala Glu Ile Asp Lys Asp Ile Glu Asn
        595                 600                 605

Phe Pro Met Gly Tyr Asp Thr Asp Ile Ser Glu His Gly Ser Ser Ile
    610                 615                 620

Ser Val Gly Gln Lys Gln Arg Leu Ser Ile Ala Arg Ser Leu Leu Thr
625                 630                 635                 640

Glu Ser Asn Val Leu Leu Phe Asp Glu Ser Thr Ser Ser Leu Asp Thr
                645                 650                 655

Ile Thr Glu Gln Arg Ile Ile Glu Asn Leu Leu Asn Leu Asn Asp Lys
            660                 665                 670

Thr Leu Ile Phe Val Ala His Arg Leu Ser Val Ala Lys Gln Thr Glu
        675                 680                 685

Asn Ile Ile Val Met Asp His Gly Gly Ile Val Glu Thr Gly Ser His
    690                 695                 700

Asp Lys Leu Ile Leu Glu Asn Gly Tyr Tyr Lys Glu Leu Cys Thr Val
705                 710                 715                 720

Lys Thr Lys Lys Lys Glu Phe
                725
```

<210> SEQ ID NO 15

-continued

<211> LENGTH: 3055
<212> TYPE: DNA
<213> ORGANISM: Lactobacillus sake

<400> SEQUENCE: 15

```
agcttcggga ttcttagcta tatcaatttt gctataaact tgggaaagaa cgtcaataat      60
atcgagtaat tcactggatt ttacaggacg cttttctagt aagtgcaaga gagcttcgat     120
gttgttttta gattcagttt taatattgtc tttgtttgcc attttaatca cgtctccttt     180
tttatagtaa taaaaaaaac acaattaaat tagtgctttt ttatctggta attaacaaac     240
tccatgaccg ccattagcta gatggttac tccacaagtc catgcttgcc cccaatttac      300
tgaacagccg tgagagttac agctaacgcc attaccatag tatttaccac ctgtaataga     360
tttcatttct tgaattgtta ggcttttttgc gttttttcata agaacatct ccaaattata    420
ttttttagtg attcttgaag ttctgttgta acgcagaatt ttggaagaat gagtacttgt     480
tagaaatttg ccgatttaaa taattaacaa accccatgac cgccattagc tagatgattt     540
accccacaag tccatgcttg ccccaattt actgaacaac catgagagtt acagctaaca     600
ccattaccat agtatttacc acctgtgatg gatttattt cttggatcgt taagctacgt     660
gtattcttca ttttgaatac ctcctgttaa ataattttta cacgatcagt gtagttctaa     720
tgtgaaattg tgtcaagttt agcaaatata tattttaggc atggaaaaac ttgcttttaa     780
ttcgacttga ctataacggt ataatactgg tattactata tttgtttagc ttcacaaaaa     840
aattaggaga cttatatatt gtttaatctg ttgagataca aaaaattata ttgttcacaa     900
gtggatgaag atgattgtgg aatcgcagct ttgaatatga ttttttaaaaa ttttggttcc     960
gaatattcac tatcaaaatt gcgattctta gcaaaaacca gtcaacaagg gactactatt    1020
tttggactga taaaggctgc agaggaacta aatttagaag cgaatgcatt acaagctgat    1080
atgggcatct ttaaagatga aaatttaatg ctaccaatca ttgcacatgt tttaaagcaa    1140
ggaaaagttc tgcattacta cgttgtattt gatgtttcga aagactttt aattattggt     1200
gacccagacc caacaatagg aattacggaa atctccaaaa aggatttga aaatgaatgg     1260
acgggtaatt tcataacatt tcaaaagga aagaactttg tttcagagaa gcagagaaat    1320
aacagtttac tcaagtttat tcctatttg agacagcaaa aatccctaat attctggata     1380
gctttcgccg caatactatt gatgataatt agtattgcag gatcactttt tttagaacaa    1440
cttgtagata tatatatacc acacaaaaat atggatacat tggggattat ctcgatttgc    1500
ttaattggag cctatctttt acaggccgta atgacgtatt ttcagaattt tttactaact    1560
atatttggac aaaatctttc tagaaaaatt attttaaatt atattaatca cctttttgaa    1620
ttacccatgt ctttcttctc aacacgtaga gttggcgaaa tagtctctcg gtttacagat    1680
gcaagcaaga ttatagatgc tttggcaagt acgattttga ctctcttttt agatgtttgg    1740
atgttggtta caatctcaat cgttctcgta tttttaaata caagttatt tatgatttct    1800
ctggtatcta taccggtgta ctcagttata atttatgcgt ttaaaaatac atttaatggc    1860
ctgaaccata atcaatgga aaatgcagca ttattgaatt ctgcaataat cgaaaacgta     1920
actggcatag aaactgtaaa atcattaact tcagaagaat tttcctacaa tcaaatcact    1980
gatagattcg aaaattttct taacagttcc ttacggtata cgatagctga ccaaggacag    2040
caagctttaa aagtgggttt gaagctaatt cttatagtct ttatcttatg ggctggagca    2100
atccaagtta tgaggggggaa tctcacagtc ggaagattat tggcttttaa tgctttagta    2160
acatactttt taaatcccctt agagaatatt attaatttac aaccaaagct acaaactgca    2220
```

-continued

```
agagtcgcta atattagact aaatgaagta ttattagtgg attctgagtt taataggggg   2280
ggacgcgaca gctcaacaaa cttaaatggg gatatcgtat ttcaagatgt agaatttagt   2340
tatggttacg gatcgaacgt attgcacaac atcaatataa aaatacaaaa gaatagtagt   2400
acaacgattg ttggtatgag cggttctggg aaatccacat tagcaaaatt aatggttggt   2460
ttctatcaag ccggatcagg acaaatatta ttaaatggta aattaatcga taacattgat   2520
cgtcatgccc tgagacaatc gattacgtat gtaccacagg aaccggtaat gttcgcaggt   2580 acaatttttag aaaatcttat tatgcagaat aaaagaaatt tatctattga taaagtgaaa   2640
gaggcatgta ggatagccga aattgataaa gatatagaaa attttcctat ggggtatgat   2700
acagatattt ccgaacatgg gagttcaatc tcagtaggtc aaaaacaaag actttctatt   2760
gcaagatcac tgctgacaga gtctaatgtt ttactgtttg atgaatcaac cagtagtttg   2820
gacactatta ctgagcagcg aataattgaa aacctattga atttaaatga caaaacatta   2880
atattcgttg cacatcgatt gtcagttgct aagcaaactg aaaatattat cgttatggat   2940
cacggtggaa ttgttgaaac aggttcgcat gataaattaa tattggaaaa tggatattat   3000
aaagaattat gtactgtgaa gacgaagaaa aaagaatttt agataaaaca aaac          3055
```

<210> SEQ ID NO 16
<211> LENGTH: 17
<212> TYPE: DNA
<213> ORGANISM: Lactobacillus sake

<400> SEQUENCE: 16

```
ccttggtcag gctatcg                                                    17
```

<210> SEQ ID NO 17
<211> LENGTH: 20
<212> TYPE: DNA
<213> ORGANISM: Lactobacillus sake

<400> SEQUENCE: 17

```
atcaccttttt tgaattaccc                                                20
```

<210> SEQ ID NO 18
<211> LENGTH: 3055
<212> TYPE: DNA
<213> ORGANISM: Lactobacillus sake

<400> SEQUENCE: 18

```
gtttttgttt tatctaaaat tcttttttct tcgtcttcac agtacataat tctttataat   60
atccattttc caatattaat ttatcatgcg aacctgtttc aacaattcca ccgtgatcca   120
taacgataat attttcagtt tgcttagcaa ctgacaatcg atgtgcaacg aatattaatg   180
ttttgtcatt taaattcaat aggttttcaa ttattcgctg ctcagtaata gtgtccaaac   240
tactggttga ttcatcaaac agtaaaacat tagactctgt cagcagtgat cttgcaatag   300
aaagtctttg ttttttgacct actgagattg aactcccatg ttcggaaata tctgtatcat   360
accccatagg aaaattttct atatctttat caatttcggc tatcctacat gcctctttca   420
ctttatcaat agataaattt cttttattct gcataataag attttctaaa attgtacctg   480
cgaacattac cggttcctgt ggtacatacg taatcgattg tctcagggca tgacgatcaa   540
tgttatcgat taatttacca tttaataata tttgtcctga tccggcttga tagaaaccaa   600
ccattaattt tgctaatgtg gatttcccag aaccgctcat accaacaatc gttgtactac   660
```

-continued

```
tattcttttg tattttata  ttgatgttgt  gcaatacgtt  cgatccgtaa  ccataactaa   720
attctacatc  ttgaaatacg  atatccccat  ttaagtttgt  tgagctgtcg  cgtcccccc    780 tattaaactc  agaatccact  aataatactt  catttagtct  aatattagcg  actcttgcag   840
tttgtagctt  tggttgtaaa  ttaataatat  tctctaaggg  atttaaaaag  tatgttacta   900
aagcattaaa  agccaataat  cttccgactg  tgagattccc  cctcataact  tggattgctc   960
cagcccataa  gataaagact  ataagaatta  gcttcaaacc  cacttttaaa  gcttgctgtc  1020
cttggtcagc  tatcgtatac  cgtaaggaac  tgttaagaaa  attttcgaat  ctatcagtga  1080
tttgattgta  ggaaaattct  tctgaagtta  atgatttac  agtttctatg  ccagttacgt  1140
tttcgattat  tgcagaattc  aataatgctg  cattttccat  tgatttatgg  ttcaggccat  1200
taaatgtatt  tttaaacgca  taaattataa  ctgagtacac  cggtatagat  accagagaaa  1260
tcataaataa  ctttgtattt  aaaaatacga  gaacgattga  gattgtaacc  aacatccaaa  1320
catctaaaaa  gagagtcaaa  atcgtacttg  ccaaagcatc  tataatcttg  cttgcatctg  1380
taaaccgaga  gactatttcg  ccaactctac  gtgttgagaa  gaaagacatg  ggtaattcaa  1440
aaaggtgatt  aatataattt  aaaataattt  ttctagaaag  attttgtcca  aatatagtta  1500
gtaaaaaatt  ctgaaaatac  gtcattacgg  cctgtaaaag  ataggctcca  attaagcaaa  1560
tcgagataat  ccccaatgta  tccatatttt  tgtgtggtat  atatatatct  acaagttgtt  1620 ctaaaaaag  tgatcctgca  atactaatta  tcatcaatag  tattgcggcg  aaagctatcc  1680
agaatattag  ggattttgc  tgtctcaaaa  taggaataaa  cttgagtaaa  ctgttatttc  1740
tctgcttctc  tgaaacaaag  ttctttcctt  ttgaaaatgt  tatgaaatta  cccgtccatt  1800
cattttcaaa  atccttttg  gagatttccg  taattcctat  tgttgggtct  gggtcaccaa  1860
taattaaaaa  gtctttcgaa  acatcaaata  caacgtagta  atgcagaact  tttccttgct  1920
ttaaaacatg  tgcaatgatt  ggtagcatta  aattttcatc  tttaaagatg  cccatatcag  1980
cttgtaatgc  attcgcttct  aaatttagtt  cctctgcagc  ctttatcagt  ccaaaaatag  2040
tagtcccttg  ttgactggtt  tttgctaaga  atcgcaattt  tgatagtgaa  tattcggaac  2100
caaaattttt  aaaatcata  ttcaaagctg  cgattccaca  atcatcttca  tccacttgtg  2160
aacaatataa  ttttttgtat  ctcaacagat  taaacaatat  ataagtctcc  taatttttt  2220 gtgaagctaa  acaaatatag  taataccagt  attataccgt  tatagtcaag  tcgaattaaa  2280
agcaagtttt  tccatgccta  aaatatatat  ttgctaaact  tgacacaatt  tcacattaga  2340
actacactga  tcgtgtaaaa  attatttaac  aggaggtatt  caaaatgaag  aatacacgta  2400
gcttaacgat  ccaagaaata  aaatccatca  caggtggtaa  atactatggt  aatggtgtta  2460
gctgtaactc  tcatggttgt  tcagtaaatt  gggggcaagc  atggacttgt  ggggtaaatc  2520
atctagctaa  tggcggtcat  ggggtttgtt  aattatttaa  atcggcaaat  ttctaacaag  2580
tactcattct  tccaaaattc  tgcgttacaa  cagaacttca  agaatcacta  aaaaatataa  2640
tttggagatg  ttctttatga  aaaacgcaaa  agcctaaca  attcaagaaa  tgaaatctat  2700
tacaggtggt  aaatactatg  gtaatggcgt  tagctgtaac  tctcacggct  gttcagtaaa  2760
ttgggggcaa  gcatggactt  gtggagtaaa  ccatctagct  aatggcggtc  atggagtttg  2820
ttaattacca  gataaaaaag  cactaattta  attgtgtttt  ttttattact  ataaaaaagg  2880
```

-continued

```
agacgtgatt aaaatggcaa acaaagacaa tattaaaact gaatctaaaa acaacatcga    2940
agctctcttg cacttactag aaaagcgtcc tgtaaaatcc agtgaattac tcgatattat    3000
tgacgttctt tcccaagttt atagcaaaat tgatatagct aagaatcccg aagct         3055
```

ANTI-*LISTERIA* BACTERIOCIN

Figure 1:
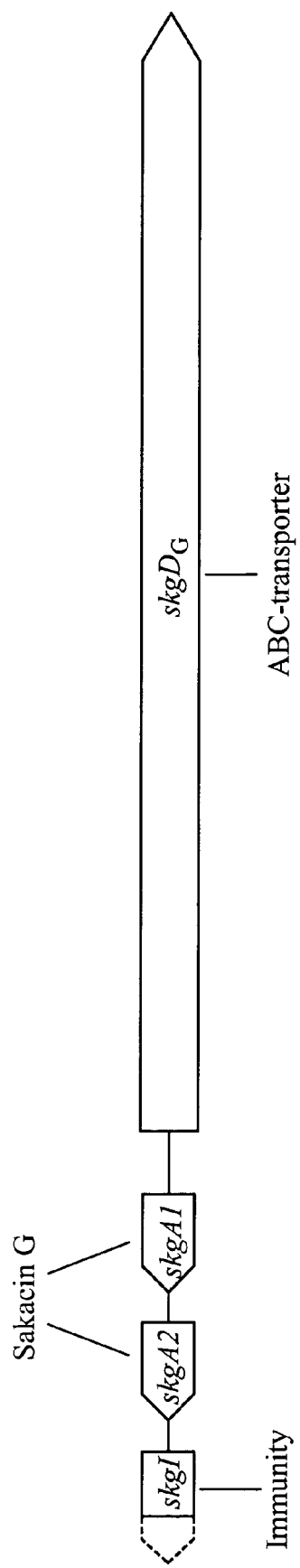

This application is a divisional application of prior application Ser. No. 10/296,723, filed Nov. 26, 2002 (now U.S. Pat. No. 6,855,518); which is a 371 national stage application of PCT/FR01/01642, filed May 28, 2001; which claims priority over French application No. FR 00 06859, filed May 29, 2000 and French application No. FR 00 13407, filed Oct. 19, 2000.

The present invention relates to a bacteriocin of *Lactobacillus sakei* and more especially of *Lactobacillus sakei* 2512, to a nucleotide sequence coding for that bacteriocin, and to the industrial use of that bacteriocin as an active agent against pathogenic or undesirable flora in the preparation of food products.

Lactic acid bacteria are used intensively in the fermentation of foods not only to improve the taste and texture of the foods but especially to prolong their storage life. Numerous lactic acid bacteria are in fact capable of inhibiting the growth of certain Gram positive bacteria, including pathogenic strains such as *Listeria monocytogenes*, thanks to the excretion of antagonistic molecules, including peptide compounds. These peptide compounds, called bacteriocins, are therefore potentially valuable for preserving fermented food products in terms of quality and health.

As examples of such bacteriocins, special mention may be made of those which form the sub-class of polypeptides called anti-*Listeria* bacteriocins, bacteriocins of class IIa (Ennahar S. et al., 2000, FEMS Microbiol. Rev., 24: 85-106) and cystibiotic bacteriocins (Jack R. et al., 1995, Microbiol. Rev., 59(2): 171-200). The potential use of one of these class IIa bacteriocins, divercin V41, for preventing the growth of *Listeria monocytogenes* in smoked salmon has recently been noted (Duffes F. et al., 1999, J. Food Prot., 62(12): 1394-1403).

The sequences of these polypeptides exhibit strong similarities in the N-terminal portions, with the presence of a disulfide bridge in particular. The hydrophobic C-terminal portion is much more variable, but some of those bacteriocins, so-called pediocin-type bacteriocins (pediocin PA-1, enterocin A and divercin V41), are characterised by a number of residues greater than 40 and the presence of a second disulfide bridge on the C-terminal side.

The authors of the present invention have discovered a new class IIa bacteriocin produced from a specific strain of *Lactobacillus sakei*, which proves to be especially effective in inhibiting the growth of *Listeria*, more especially of *Listeria monocytogenes*.

In agreement with Tagg J. R. et al., Bacteriol. Rev., 40: 722-756 (1976), the term "bacteriocin" within the scope of the invention refers to a polypeptide produced, by ribosome synthesis, from microorganisms capable of inhibiting specifically the growth of other bacteria.

The present invention therefore relates in the first instance to a polypeptide derived from the strain *Lactobacillus sakei* 2512, having bacteriocin activity.

The strain *Lactobacillus sakei* 2512 was deposited on May 23, 2006 with the Collection Nationale De Cultures De Micro-organismes (CNCM) (National Collection of Microorganism Cultures), where it is registered under deposit number 1-2479.

The bacteriocin to which the present invention relates has been named sakacin G. It is a polypeptide having a molecular mass of the order of from 3700 to 3900 and preferably of about 3834 Da, determined by mass spectrometry. It has a bacterial inhibition spectrum which is very similar to that of the class IIa bacteriocins. Accordingly, it proves to be especially effective against the strains of *Lactobacillus sakei* other than *Lactobacillus sakei* 2512, *Pediococcus cerevisiae*, the totality of the *Listeria* strains and against *Enterococcus faecalis* and *Enterococcus durans*. By contrast, it proves to be inactive against the other species of *Lactobacillus* such as, for example, *Lactobacillus debrueckii*, *Lactobacillus plantarum*, *Lactobacillus brevis*, *Lactobacillus casei* and a strain of *Enterococcus faecium*.

Like the anti-Listeria bacteriocins of the pediocin type, sakacin G advantageously possesses two disulfide bridges in its peptide structure.

An analysis of the genetic determinants of several class IIa bacteriocins has shown that the genes involved in their production, transport and immunity are organised into one or more operon-type structures. These operons are often located in a plasmid and generally possess at least two genes coding for proteins, homologous to an ABC transporter and an accessory protein, probably involved in bacteriocin export.

Cloning of the nucleotide fragment containing the sakacin G gene has revealed the existence of three complete open reading frames skgA1 (SEQ ID NO: 1), skgA2 (SEQ ID NO: 3) and skgDc (SEQ ID NO: 13) (including the truncated reading frame skgD (SEQ ID NO: 7)) and a truncated frame skgI (SEQ ID NO: 5), a diagrammatic representation of which is shown in FIG. 1. The nucleotide fragment is a double strand, the 5'-3' single strand of which is shown in SEQ ID NO: 15.

The products of the genes skgA1 and skgA2, called pre-bacteriocins, may undergo maturation during which their respective leader peptides are cleaved between residues 18 and 19, thus liberating active sakacin G (residues 19-55).

The 5'-3' single-strand nucleotide fragment comprising skgA1, skgA2, skgD and skgI appears in SEQ ID NO: 9.

The present invention accordingly relates also to an isolated polypeptide corresponding to a bacteriocin, characterised in that it comprises SEQ ID NO: 2 and/or SEQ ID NO: 4. The sequence of the mature bacteriocin corresponds to SEQ ID NO: 12 and is comprised in SEQ ID NOs: 2 and 4.

The reading frame called skgI codes for a protein of 52 residues. A comparison of that sequence with the database sequence shows strong similarities between SkgI and so-called immunity proteins. It probably codes for the immunity protein protecting the sakacin-G-producing bacterium.

The present invention extends also to an isolated polypeptide comprising SEQ ID NO: 6 corresponding to the reading frame skgI.

With regard to the last gene skgDc, it codes for a protein which is homologous with proteins of the ABC transporter family, and more especially of the transporter of pediocin PA-1. The gene skgDc probably codes for the ABC transporter specific to sakacin G.

The present invention extends also to the isolated polypeptide comprising SEQ ID NO: 8 corresponding to the so-called skgD gene, and to the isolated polypeptide comprising SEQ ID NO: 14 corresponding to the so-called skgDc gene.

It will be understood that homologous sequences are also included, which sequences are defined as
  i) sequences that are similar to at least 70% of SEQ ID NO: 2, 4, 6, 8, 12, or 14; or
  ii) sequences coded for by a homologous nucleic acid sequence as defined hereinbelow, that is to say a nucleic acid sequence that hybridises with SEQ ID NO: 1, 3, 5, 7, 9, 13 or 15 or its complementary sequence, under stringent hybridisation conditions.

There too, the term "similar" refers to perfect resemblance or identity between the amino acids of the homologous sequences under comparison, but also to non-perfect resemblance, which is referred to as similarity. This search for similarities in a polypeptide sequence takes into account conservative substitutions, which are substitutions of amino acids of the same class, such as substitutions of amino acids in non-charged side chains (such as asparagine, glutamine, serine, threonine and tyrosine), of amino acids in basic side chains (such as lysine, arginine, histidine), of amino acids in acid side chains (such as aspartic acid and glutamic acid); of amino acids in non-polar side chains (such as glycine, alanine, valine, leucine, isoleucine, proline, phenylalanine, methionine, tryptophan and cysteine).

More generally, therefore, "homologous amino acid sequence" is understood as being any amino acid sequence that differs from SEQ ID NO: 2, 4, 6, 8, 12, or 14 by substitution, deletion and/or insertion of an amino acid or of a reduced number of amino acids, especially by substitution of natural amino acids by non-natural amino acids or pseudo-amino acids in positions such that these modifications do not significantly affect the biological activity of the isolated polypeptide and preferably of sakacin G.

Such a homologous amino acid sequence is preferably similar to at least 85% of SEQ ID NO: 2, 4, 6, 8, 12, or 14, preferably at least 95%.

Homology is generally determined using sequence analysis software (for example Sequence Analysis Software Package of the Genetics Computer Group, University of Wisconsin Biotechnology Center, 1710 University Avenue, Madison, Wis. 53705). Similar amino acid sequences are aligned in order to obtain the maximum degree of homology (i.e. identity or similarity, as defined above). To that end, it may be necessary to introduce gaps into the sequence artificially. Once optimum alignment has been achieved, the degree of homology is established by recording all the positions in which the amino acids of the two sequences under comparison are identical, relative to the total number of positions.

The biological activity of the isolated polypeptide, and especially of sakacin G, refers to its capacity to inhibit the growth of undesirable and/or pathogenic bacterial strains, preferably of *Listeria* bacteria and more especially of *Listeria monocytogenes* bacteria.

The present invention relates also to an isolated nucleic acid coding for a polypeptide as defined above.

More precisely, the present invention relates to an isolated nucleic acid comprising SEQ ID NO: 1 and/or SEQ ID NO: 3.

Figure 2:
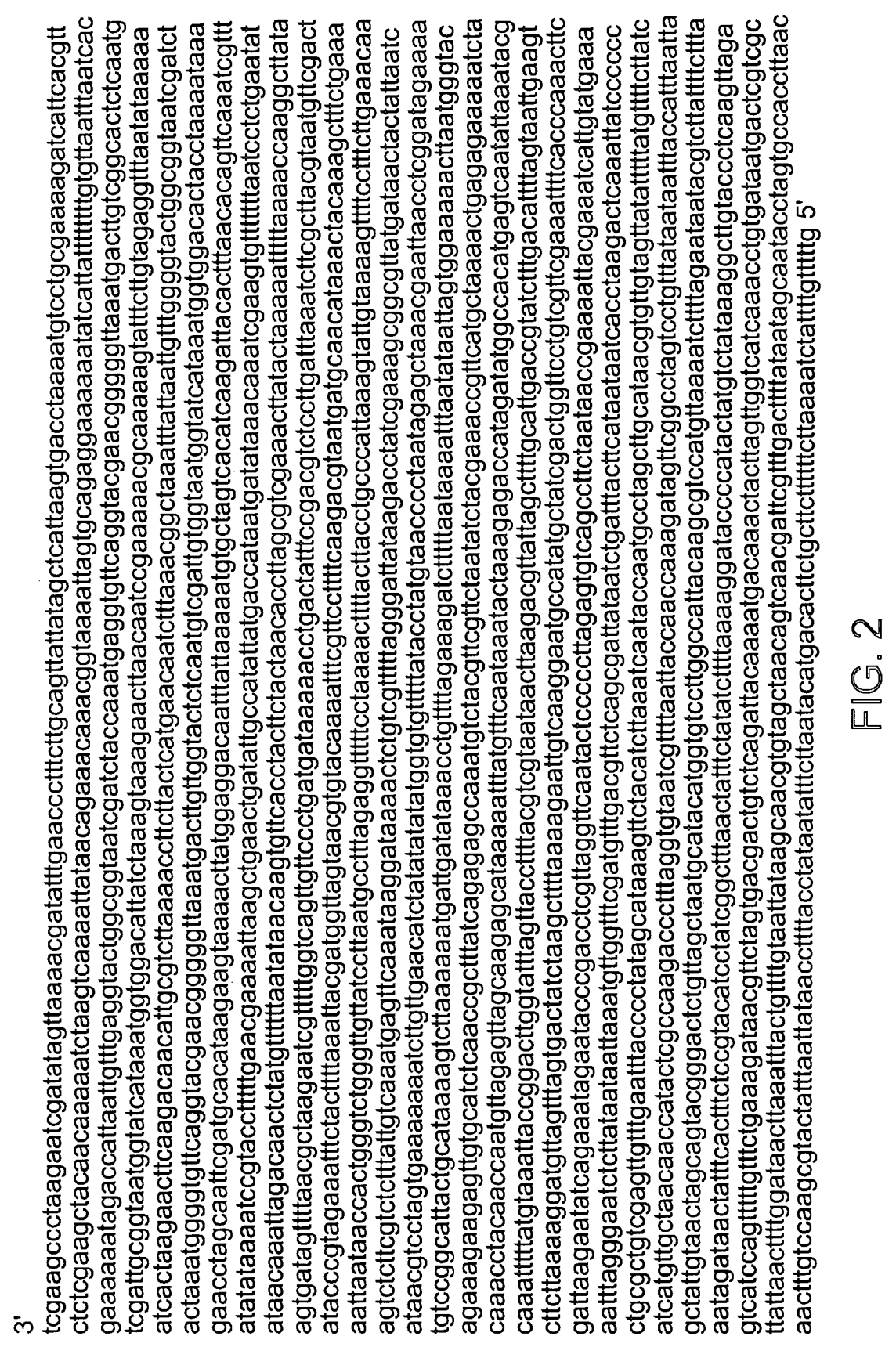

The complete nucleotide sequence of the region involved in the expression of sakacin G (3055 bp) has been determined. It is a double-strand DNA whose 5'-3' strand is shown in SEQ ID NO: 15. The 3'-5' strand is shown in FIG. 2. The present invention relates also to a nucleic acid comprising such a sequence.

As described above, this sequence has three complete open reading frames skgA1, skgA2 and skgDc and a truncated frame skgI. The supposed genes skgA1 (SEQ ID NO: 1), skgA2 (SEQ ID NO: 3) and skgI (SEQ ID NO: 5) are oriented therein in the opposite direction relative to skgDc (SEQ ID NO: 13).

Within the scope of the present invention there are also claimed the nucleic acid comprising SEQ ID NO: 5, the nucleic acid comprising SEQ ID NO: 13 and the nucleic acid comprising SEQ ID NO: 7.

It will be understood that homologous sequences are also included, which sequences are defined as:

i) sequences that are similar to at least 70% of SEQ ID NO: 1, 3, 5, 7, 9, 13, or 15; or ii) sequences that hybridise with SEQ ID NO: 1, 3, 5, 7, 9, 13, or 15 or their complementary sequence, under stringent hybridisation conditions; or iii) sequences coding for the polypeptide named sakacin G, as defined above.

A homologous nucleotide sequence according to the invention is preferably similar to at least 75% of the SEQ ID NO: 1, 3, 5, 7, 9, 13, or 15, preferably at least 85% or at least 90%.

Such a homologous nucleotide sequence preferably hybridises specifically with the complementary sequences of SEQ ID NO: 1, 3, 5, 7, 9, 13, or 15 under stringent conditions. The parameters defining the stringency conditions depend on the temperature at which 50% of the coupled strands separate (Tm).

For sequences comprising more than 30 bases, Tm is defined by the equation (Sambrook et al., 1989, NY: Cold Spring Harbor Laboratory):

$$Tm=81.5+0.41(\% \ G+C)+16.6 \ \text{Log(cation concentration)}-0.63(\% \ \text{formamide})-(600/\text{number of bases})$$

For sequences having a length less than 30 bases, Tm is defined by the equation:

$$Tm==4(G+C)+2(A+T).$$

Under appropriate stringency conditions, under which the a specific sequences do not hybridise, the hybridisation temperature may preferably be from 5 to 10° C. below Tm, and the hybridisation buffers used are preferably solutions of high ionic strength, such as a 6×SSC solution, for example.

The expression "similar sequences" used above refers to perfect resemblance or identity between the nucleotides under comparison, but also to non-perfect resemblance, which is referred to as similarity. This search for similarities in nucleic sequences distinguishes, for example, purines and pyrimidines.

A homologous nucleotide sequence having the open reading frames shown in SEQ ID NO: 1, 3, 5, 7, 9, 13, or 15 therefore includes any nucleotide sequence which differs from sequence SEQ ID NO: 1, 3, 5, 7, 9, 13, or 15 by mutation, insertion, deletion or substitution of one or more bases, or by the degeneracy of the genetic code, insofar as it codes for a polypeptide having the biological activity of sakacin G, as defined hereinbelow.

Such homologous sequences include sequences of the genes of bacteria other than *Lactobacillus*, coding for sakacin G.

The polypeptides of the present invention can be synthesised by any method known to the person skilled in the art. The polypeptides of the invention may, for example, be synthesised by techniques of the chemistry of synthesis, such as Merrifield-type synthesis, which is advantageous for reasons of purity, of antigen specificity, of the absence of undesirable secondary products and of ease of production.

The present invention relates also to a process for the production of a recombinant polypeptide, in which a vector comprising a nucleic acid according to the present invention is transferred into a host cell which is cultured under conditions permitting the expression of a polypeptide according to the present invention or of a polypeptide coded for by a nucleic acid sequence according to the present invention.

The recombinant bacteriocin may also be produced by a process in which a vector containing a nucleic acid comprising a nucleotide sequence according to the invention, and preferably SEQ ID NO: 1 and/or 3 or a homologous sequence, is transferred into a host cell which is cultured under conditions permitting the expression of the corresponding polypeptide. The resulting protein can then be recovered and purified. The purification processes used are known to the person skilled in the art. The resulting recombinant polypeptide can be purified starting from lysates and cell extracts, from the supernatant of the culture medium, by methods used individually or in combination, such as fractionation, methods of chromatography, techniques of immunoaffinity with the aid of specific monoclonal or polyclonal antibodies, etc.

The nucleic acid sequence of interest, coding for sakacin G, can be inserted into an expression vector in which it is linked in an operative manner to elements permitting regulation of its expression, such as, especially, promoters, activators and/or transcription terminators. The signals controlling the expression of the nucleotide sequences (promoters, activators, termination sequences, etc.) are chosen depending on the cell host used. To that end, the nucleotide sequences according to the invention can be inserted into vectors which replicate autonomously within the chosen host, or vectors which integrate in the chosen host. Such vectors will be prepared by the methods conventionally used by the person skilled in the art, and the clones resulting therefrom can be introduced into a suitable host by standard methods, such as, for example, electroporation or calcium phosphate precipitation.

The cloning and/or expression vectors as described above, containing a nucleotide sequence defined according to the invention, also form part of the present invention.

The invention relates also to the host cells transformed, temporarily or permanently, by those expression vectors. These cells can be obtained by introducing into host cells, preferably prokaryotic host cells, a nucleotide sequence inserted into a vector as defined above, then culturing said cells under conditions permitting the replication and/or expression of the transferred nucleotide sequence.

Examples of host cells include especially bacteria such as *Lactococcus, Lactobacillus, Leuconostoc, Streptococcus, Pediococcus, Escherichia* and yeasts.

The nucleotide sequences of the invention may be of synthetic or natural origin. They may be DNA or RNA sequences obtained by the screening of sequence libraries by means of probes produced on the basis of the sequences SEQ ID NO: 1, 3, 5, 7, 9, 13, and/or 15. Such libraries can be prepared by conventional techniques of molecular biology known to the person skilled in the art.

The nucleotide sequences according to the invention can also be prepared by chemical synthesis, or alternatively by mixed methods including the chemical or enzymatic modification of sequences obtained by the screening of libraries.

The present invention relates also to a method of inhibiting the growth of *Listeria*, more especially of *Listeria monocytogenes*, in an environment which may or may not be a food environment and which is susceptible to contamination by *Listeria monocytogenes*.

*Listeria monocytogenes* are pathogenic microorganisms which are the source of severe diseases in humans and animals and which especially can easily be transmitted by contaminated foods, more especially by means of meat, meat products, seafood products, milk and products derived therefrom. The present invention therefore proposes a method of inhibiting the growth of *Listeria monocytogenes* in a food likely to contain *Listeria monocytogenes* as a contaminant, said process comprising the addition of a polypeptide according to the invention to said food in an amount sufficient to inhibit the growth of *Listeria monocytogenes*.

The bacteriocins according to the invention are preferably used in any food system in an amount of from 1 to 100,000 arbitrary units (AU) of bacteriocins per gram of food.

An AU of bacteriocins is defined as 5 µl of the highest dilution of the culture supernatant leading to a defined growth inhibition zone, relative to a control strain of a Gram positive bacteria, on an agar medium.

Although foods are most affected by *Listeria monocytogenes* contamination, veterinary and medical products can also be contaminated with this type of bacteria, as can cosmetic products or similar products.

The bacteriocins according to the present invention, and especially sakacin G, can therefore also be used to inhibit the growth of this type of pathogen in such products.

Accordingly, the present invention relates to the use of a bacteriocin according to the present invention as an active agent against pathogenic or undesirable flora, especially in the preparation of food products, and more precisely to inhibit the growth and propagation of *Listeria*, more especially of *Listeria monocytogenes*, in food products.

The polypeptide can be incorporated as such into the food product in question, or alternatively it can be produced therein from the strain *Lactobacillus sakei* 2512.

Accordingly, the present invention relates also to the use of the strain *Lactobacillus sakei* 2512 in a food product to generate therein a bacteriocin polypeptide according to the invention.

The invention relates also to a bacteriocin composition, characterised in that it comprises at least one polypeptide according to the present invention, that is to say derived from the strain *Lactobacillus sakei* 2512 or comprising SEQ ID NO: 2, 4, 12, or 14 or the strain *Lactobacillus sakei* 2512.

The invention extends also to the use of the strain *Lactobacillus sakei* 2512 intended to produce a polypeptide as defined above, for inhibiting the growth and propagation of *Listeria*, more especially of *Listeria monocytogenes*, in food products, and the compositions comprising that strain.

The Examples and the Figure below are given by way of example and do not limit the subject-matter of the present invention.

FIGURE

FIG. 1: Diagrammatic representation of the genetic locus involved in the production of sakacin G.

FIG. 2: Complimentary 3'-5' strand (SEQ ID NO: 18) corresponding to the complete nucleotide sequence of the region involved in the expression of sakacin G and the 5'-3' strand of which is shown in SEQ ID NO: 15.

MATERIALS AND METHODS

Bacterial strains and culture media. *Lactobacillus sakei* 2512 is cultured at 30° C. in MRS medium (DIFCO Laboratories) sterilised for 12 minutes at 110° C. The indicator strains are cultured in BHI medium (brain-heart infusion; DIFCO Laboratories) at 37° C.

Test of activity. BHI medium, supplemented with 10 g/l agar, is inoculated at 1% with a preculture of the indicator strain in stationary phase before being poured into a Petri dish. 50 microlitres of sakacin G solution are placed in wells formed in cooled agar with a hole punch. The bacteriocin activity manifests itself in the appearance of inhibition zones around the wells after incubation overnight at 37° C.

Protein analysis. Sakacin G is analysed by mass spectrometry using a Perkin-Elmer Sciex API 165 device equipped with an Ionspray ionisation source. After lyophilisation, the active HPLC fraction is taken up in an acetonitrile/water solution (1:1) containing 0.1% formic acid, and then injected by infusion at a rate of 5 µl/minute.

The protein concentration is determined by the bicinchoninic acid method by means of the BCA kit (Sigma) according to the manufacturer's instructions.

Protein sequence comparisons are carried out using the BLAST (1) program, obtainable from the ExPASy server of the Swiss Institute of Bioinformatics.

Molecular cloning and transformation. The plasmids are extracted and purified from strains of *Escherichia coli* and *Lactobacillus sakei* 2512 according to the methods previously described by Sambrook et al., 1989, NY: Cold Spring Harbor Laboratory and Muriana and Klaenhammer, 1987, Appl. Environ. Microbiol., 53: 553-560, respectively.

The DNA restriction and modification enzymes are used according to the supplier's instructions (Gibco-BRL). Analytical and preparative agarose gel electrophoreses are carried out in Tris/borate/EDTA buffer (pH 8.3) according to the methods described by Sambrook et al., 1989, NY: Cold Spring Harbor Laboratory. The digested DNA fragments are purified starting from agarose gels using the "Prep-a-Gene" kit (Bio-Rad). Cloning in plasmids pGEM-T (Promega) and pZERO2 (Invitrogen) is carried out in accordance with the suppliers' recommendations. Southern-type transfer is carried out on nylon membrane (Hybond-N+, Amersham) according to Sambrook et al., 1989, NY: Cold Spring Harbor Laboratory. The transfer is followed by hybridisation using a radioactive probe obtained by $^{32}$P labelling with the aid of a "random primers DNA labelling system" kit (Gibco-BRL). The *E. coli* bacteria are rendered competent and transformed according to the method of Hanahan, 1983, J. Mol. Biol. 166: 557-580.

Taq polymerase (Gibco-BRL) is used according to the supplier's recommendations. Amplification of the DNA fragment coding for sakacin G was carried out with the aid of a "Geneamp 9700®" device (Perkin-Elmer) under the following conditions: 35 denaturing cycles at 94° C. for 30 seconds, hybridisation at 45° C. for 30 seconds and elongation at 72° C. for 1 minute, followed by an additional elongation cycle at 72° C. for 5 minutes.

The DNA fragment carrying the sakacin G locus is sequenced with the aid of an ABI Prism 310® automatic sequencer (Perkin-Elmer) using the "Big-dye terminator®" sequencing kit (Perkin-Elmer) and the appropriate nucleotide primers.

EXAMPLE 1

Isolation and Purification of Sakacin G

A 16 h culture of *Lactobacillus sakei* 2512 (100 ml) is centrifuged at 6000 g for 15 minutes. The culture supernatant is then heated at 70° C. for 20 minutes. The cooled supernatant is then diluted with 1 volume of water (the pH of the diluted solution must be below 6, by addition of 1M HCl if necessary) before being passed over a column (2.5× 18 cm) containing a cation-exchange resin (carboxymethylcellulose; Cellufine C-200, Amicon) equilibrated with water. After washing in succession with water (100 ml) and then with a 0.1M NaCl solution (150 ml), the sakacin G is eluted with a 0.5M NaCl solution (200 ml). The pH of all the solutions must be below 6. The active fraction is then deposited on a solid-phase extraction cartridge (Sep-pak plus C18, Waters) equilibrated in water. After washing in succession with 5 ml of 20 mM ammonium acetate solutions containing 0, 10, 20 and 30% acetonitrile, the sakacin G is eluted with 10 ml of 20 mM ammonium acetate containing 80% acetonitrile. After lyophilisation, the extract is dissolved in 1 ml of 40% aqueous acetonitrile solution and then injected onto a C8 reverse phase analytical HPLC column (Kromasil, 5 µm, 100 Å, 4.6×250 mm, A.I.T.). The HPLC was carried out on an apparatus comprising a Perkin-Elmer series 200 LC pump connected to a Perkin-Elmer 785A detector. The absorption chromatogram is recorded at 220 nm. Separation is carried out, at a rate of 0.8 ml/minute, according to the following gradient: solvent A=water/0.1% trifluoro-acetic acid; solvent B=acetonitrile/water/0.07% trifluoroacetic acid. After washing for 5 minutes with 20% of solvent B, elution is carried out by a gradient of from 20 to 40% of solvent B in 10 minutes then from 40 to 55% of solvent B in 20 minutes.

The fraction corresponding to the peak at 23 minutes proved to be active against *Listeria ivanovii* BUG 496 and was analysed by "ionspray" ionisation mass spectrometry. The molecule appears at least 95% pure and has a molecular mass of 3834.32±0.31 Da. The quantity of sakacin G so purified was estimated at 120 µg from 100 ml of culture. The purification yield was estimated at 55% of activity found.

Part of the primary sequence of sakacin G was determined by microsequencing and two degenerate oligonucleotides were established starting from that sequence.

EXAMPLE 2

Cloning of the Genetic Locus Involved in the Production of Sakacin G

By reverse genetics, two degenerate oligonucleotides SakG01 (5' AARTATTATGGNAAYGGNGT 3') (SEQ ID NO: 10) and SakG02S (5' ACATGATGNCCNCCRTTNGC 3') (SEQ ID NO: 11) were chosen in order to amplify the DNA fragment corresponding to the structural gene of mature sakacin G (SEQ ID NO: 15) by polymerase chain reaction (PCR). The amplified product so obtained, having an approximate size of 100 bp, was cloned in plasmid pGEM-T to form plasmid pJMBYC01. The restriction fragment PvuII of 560 bp, derived from pJMBYC01, including the inserted fragment, was used as the hybridisation probe during a Southern-type transfer for locating the structural gene on the genome of *Lactobacillus sakei* 2512. Starting from a plasmid extract of *Lb. sakei* 2512 digested by the restriction enzymes HindIII and EcoRI, the probe revealed fragments having sizes of approximately 2.1 and 9 kbp, respectively. The fragment HindIII of 2.1 kbp was purified and then inserted into the vector pZERO2 in order to yield the plasmid pJMBYC02. The presence of the structural gene of sakacin G in pJMBYC02 was demonstrated by PCR amplification with the primers SakG01 and SakG02 and then by nucleotide sequencing of the fragment inserted in pJMBYC02. A similar strategy was used to determine the complete sequence of the gene skgD. The plasmid extract of *Lb. sakei* 2512 was digested by XbaI. The digestion product was inserted into plasmid pBluescript SK+. The clones carrying the sequence of interest were revealed by means of a radioactive probe prepared by PCR carried out on plasmid pJMBYC02 with the aid of the oligonucleotides SakG03 (5'CCTTGGTCAGGCTATCG 3') (SEQ ID NO: 16) and SakG04 (5' ATCACCTTTTTGAATTACCC 3') (SEQ ID NO: 17).

Analysis of the complete nucleotide sequence of the region (3051 bp) revealed the existence of three complete open reading frames skgA1 and skgA2 and skgDc and a truncated frame skgI. The supposed genes skgA1, skgA2 and skgI are oriented in the opposite direction relative to skgD.

Each of the open reading frames is preceded by a potential ribosome fixing site. The genes skgA1 and skgA2 both code for proteins having 55 amino acid residues, the sequences 19-55 of which are completely identical. Sequence 19-52 corresponds to the sequence of sakacin G obtained by microsequencing. The presence of 4 cysteine residues in positions 9, 14 and 24 and in the C-terminal position is to be noted. Moreover, the calculated molecular mass of this peptide, 3838.2 Da, which differs from the measured molecular mass (3834.32 Da) by 4 Da, shows the presence of two disulfide bridges in sakacin G, as has already been demonstrated for other anti-*Listeria* bacteriocins. Sequences 1-18 of the proteins SkgA1 and SkgA2 differ by only 3 residues and have strong homologies with the "leader" peptides of the class II bacteriocins, which are involved in the transport of those peptides by specific ABC transporters. In particular, the terminal GG unit is characteristic of these leader sequences and constitutes the maturation site of these bacteriocins. A comparison of the nucleotide sequences of the genes skgA1 and skgA2 also shows an identity of sequence of more than 95% for the portion of the genes coding for the mature bacteriocin.

The incomplete open reading frame called skgI codes for a protein of 52 residues. A comparison of that sequence with the database sequences shows strong homologies between SkgI and the so-called immunity proteins LccI and MesI. The involvement of MesI in protection with respect to mesentericin Y105 has been demonstrated. It may be assumed that skgI codes for the sakacin G immunity protein.

The last gene skgDc codes for a protein of 727 amino acids. According to the databases, SkgDc is highly homologous with proteins of the ABC transporter family and more especially with transporters of pediocin PA-1: PedD or PapD (Marugg et al., 1992; Appl. Environ. Microbiol. 58, 2360-2367; Motlagh et al., 1994, Lett. Appl. Microbiol. 18, 305-312), of sakacin P: SppT (Huhne et al., 1996, Microbiology 142, 1437-1448), of sakacin A: SapT (Axelsson and Holck, 1995, J. Bacteriol. 177, 2125-2137) and of mesentericin Y105: MesD (Fremaux et al., 1995, Microbiology 141, 1637-1645).

EXAMPLE 3

Inhibition Spectrum

The sakacin G sensitivity of 17 bacterial strains was tested by the well test method (see Materials and Methods). The results are shown in Table 1 below:

TABLE 1

|  | Radius of the inhibition halos (mm) |
|---|---|
| Lc. lactis ATCC11454 | 0 |
| Ln. Paramesenteroides DSM 20288 | 0 |
| Ln. Mesenteroides DSM 20484 | 0 |
| Ln. Mesenteroides DSM 20240 | 0 |
| Lb. Delbrueckii DSM 20081 | 0 |
| Lb. Plantarum DSM 20174 | 0 |
| Lb brevis DSM 20054 | 0 |
| Lb. casei DSM 20011 | 0 |
| Lb. sakei 2515 | 1 |
| P. acidilactici ENSAIA 583 | 0 |
| P. cerevisiae IP 5492 | 1 |
| E. faecium ENSAIA 631 | 0 |
| E. faecalis IP 5430 | 2 |
| E. faecalis ENSAIA 636 | 1 |
| E. durans ENSAIA 630 | 2 |
| L. inocua 8811 | 3 |
| L. ivanovi BUG 496 | 6 |

The inhibition spectrum of this bacteriocin appears to be quite narrow and limited to the strains *Lactobacillus sakei* and *Pediococcus cerevisiae* for the lactic acid bacteria. Like the other class IIa bacteriocins, this peptide appears to be active against all the *Listeria* strains tested, as well as against *Enterococcus faecalis* and *Enterococcus durans*, but not against *Enterococcus faecium*.

The invention claimed is:

1. An isolated strain *Lactobacillus sakei* 2512 deposited on May 23, 2000 with the Collection Nationale De Cultures De Micro-organismes (CNCM), Institut Pasteur, France, under deposit number I-2479.

2. A bacteriocin composition that comprises the strain *Lactobacillus sakei* 2512 deposited on May 23, 2000 with the Collection Nationale De Cultures De Micro-organismes (CNCM), Institut Pasteur, France, under deposit number I-2479.

3. A method for inhibiting the growth and propagation of *Listeria* in a food product, which method comprises incorporating the strain *Lactobacillus sakei* 2512 deposited on May 23, 2000 with the Collection Nationale De Cultures De Micro-organismes (CNCM), Institut Pasteur, France, under deposit number I-2479 in the food product to generate a bacteriocin activity against *Listeria*.

* * * * *